United States Patent [19]

Chu et al.

[11] Patent Number: 4,587,967
[45] Date of Patent: May 13, 1986

[54] OXYGEN ENRICHED RECIPROCATING PISTON RESPIRATOR

[75] Inventors: Raymond D. Chu, Boulder; Anthony C. Rubner, Arvada; Marc A. Bergman, Lafayette, all of Colo.

[73] Assignee: Lifecare Services, Inc., Boulder, Colo.

[21] Appl. No.: 753,334

[22] Filed: Jul. 9, 1985

[51] Int. Cl.$^4$ ............................................. A61M 16/00
[52] U.S. Cl. ........................... 128/204.21; 128/205.11; 128/205.18
[58] Field of Search ..................... 128/203.14, 203.25, 128/204.18, 204.21, 204.22, 205.11, 205.18; 137/486, 605, 897; 364/509, 510

[56] References Cited

U.S. PATENT DOCUMENTS

| | | | |
|---|---|---|---|
| 2,403,508 | 7/1946 | Deming | 128/204.29 |
| 3,308,817 | 3/1967 | Seeler | 128/203.25 |
| 3,362,404 | 1/1968 | Beasley | 128/200.21 |
| 3,385,295 | 5/1968 | Beasley | 128/204.25 |
| 3,605,785 | 9/1971 | Dobritz | 137/101 |
| 3,675,649 | 7/1972 | Basham et al. | 128/205.11 |
| 3,734,092 | 5/1973 | Kipling | 128/203.25 |
| 3,834,383 | 9/1974 | Weigl et al. | 128/204.26 |
| 3,882,882 | 5/1975 | Preisig | 137/98 |
| 3,896,837 | 7/1975 | Robling | 137/110 |
| 3,973,579 | 8/1976 | Ollivier | 137/100 |
| 4,044,763 | 8/1977 | Bird | 128/204.26 |
| 4,064,891 | 12/1977 | Eberhardt | 137/98 |
| 4,085,766 | 4/1978 | Weigl et al. | 137/88 |
| 4,127,121 | 11/1978 | Westenskow et al. | 128/203.14 |
| 4,204,536 | 5/1980 | Albarda | 128/204.22 |
| 4,215,409 | 7/1980 | Strowe | 128/204.22 |
| 4,215,681 | 8/1980 | Zalkin et al. | 128/204.21 |
| 4,336,590 | 6/1982 | Jacq et al. | 128/204.21 |
| 4,340,044 | 7/1982 | Levy et al. | 128/205.11 |
| 4,345,612 | 8/1982 | Koni et al. | 128/204.21 |
| 4,380,233 | 4/1983 | Caillot | 128/204.21 |
| 4,425,805 | 1/1984 | Ogura et al. | 128/725 |

Primary Examiner—Kyle L. Howell
Assistant Examiner—Daniel Haneiwich
Attorney, Agent, or Firm—William C. Cochran, II

[57] ABSTRACT

A variable flow reciprocating piston respirator system which is capable of providing a substantially constant oxygen enrichment over an entire inspiration stroke of a variable flow respirator output. A proportional control valve is used to deliver oxygen from an oxygen supply tank to the output of a reciprocation piston pump. A microprocessor controls the magnitude of opening of the proportional valve to insure that a proper overall volume of the output is produced with the proper percentage of enrichment of oxygen.

17 Claims, 10 Drawing Figures

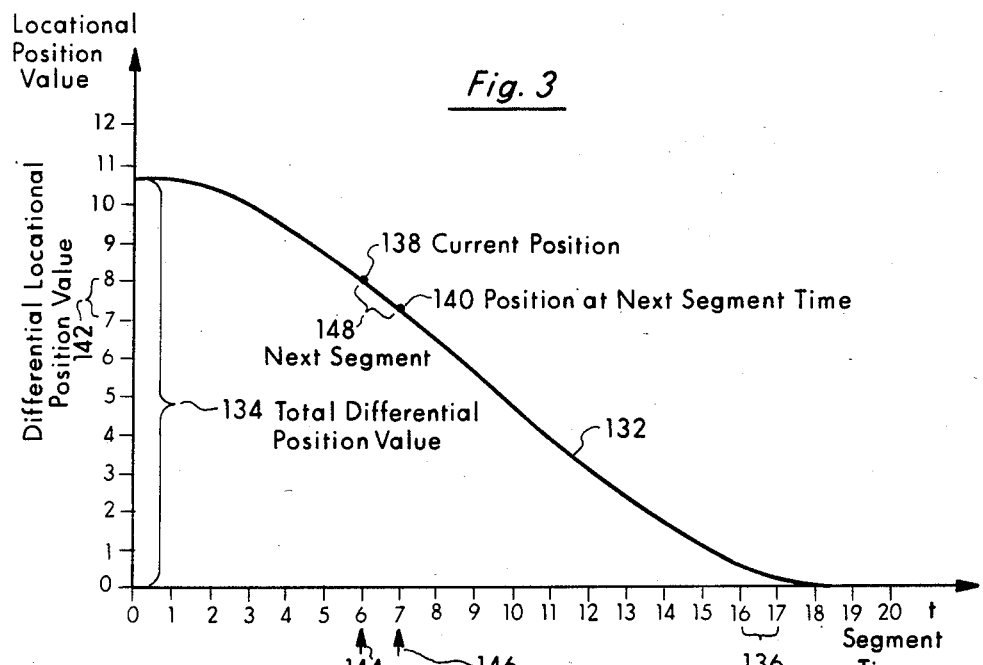
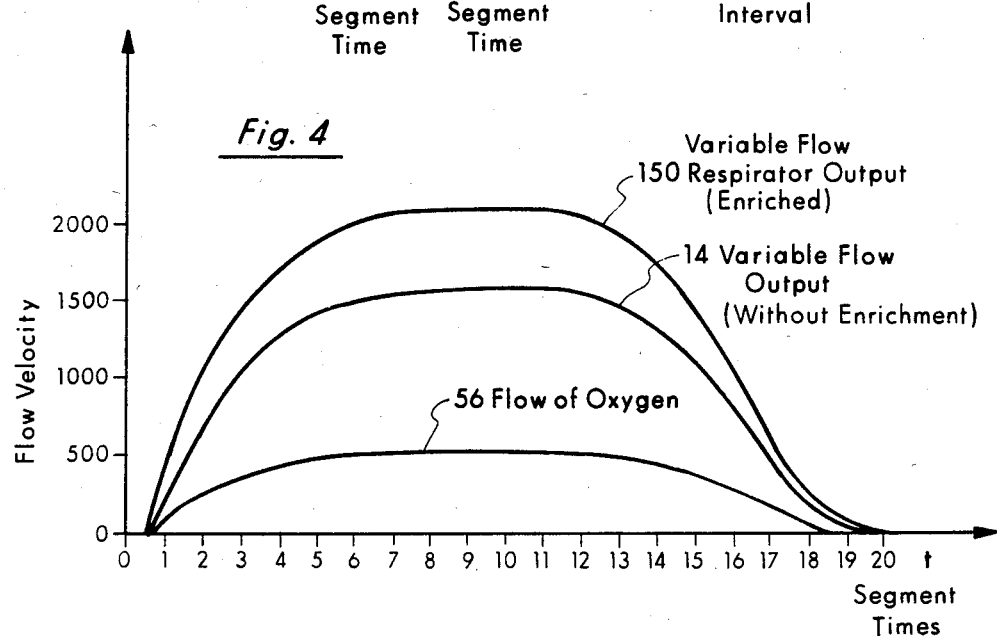

OXYGEN ENRICHED RECIPROCATING PISTON RESPIRATOR

BACKGROUND OF THE INVENTION

1. Field of Invention

The present invention pertains generally to variable flow reciprocating piston respirators and more particularly to variable flow reciprocating piston respirators with oxygen enrichment.

2. Description of the Background

Many times, patients who use respirator devices require a respirator output flow which is oxygen enriched. For variable flow reciprocating piston respirator systems, this requires the addition of oxygen to the system after, or downstream from, a piston pump which produces a variable flow output. The necessity for downstream addition of oxygen to the system is a result of various health and safety hazards associated with insertion of oxygen into the piston pump. For example, contamination of the oxygen supply can occur by insertion of oxygen into the piston pump. Additionally, insertion of a pure source of oxygen into an electromechanical device, such as a piston pump is considered extremely dangerous because of the hazards associated with fire or explosion as a result of ignition of the oxygen in the electromechanical device. Hence, government regulations have prevented insertion of an oxygen source into the piston pump of reciprocating piston respirators where elaborate sealed chambers are not provided in the devices.

To overcome these problems, conventional oxygen enrichment respirator devices have added oxygen to the respirator system downstream from the piston pump. Oxygen can be supplied from a compressed oxygen tank or other source of oxygen. The problem with such systems, however, is that the oxygen source supplies a constant flow of oxygen to the system while the reciprocating piston respirator provides a variable flow. Consequently, the percentage of oxygen enrichment over a single inspiration stroke varies greatly because of the variable flow output of the piston pump. In other words, if a sinusoidally shaped variable output flow is produced by the piston pump during a single inspiration stroke, the percentage of oxygen is extremely high during the beginning and end of the inspiration stroke, and relatively low during the middle of the stroke.

The problem of mixing two gases to obtain a substantially constant proportion of the gases has been addressed in a number of different technical arts. Pre-examination patentability searches were performed which uncovered the following patents.

| U.S. Pat. No. | Inventor | Issue Date |
|---|---|---|
| 2,403,508 | Deming | 7-9-46 |
| 3,308,817 | Seeler | 3-14-67 |
| 3,675,649 | Basham et al. | 7-11-72 |
| 3,896,837 | Robling | 7-29-75 |
| 4,204,536 | Albarda | 5-27-80 |
| 4,215,409 | Strowe | 7-29-80 |
| 4,215,681 | Zalkin et al. | 8-5-80 |
| 4,345,612 | Koni et al. | 8-24-82 |
| 4,380,233 | Caillot | 4-19-83 |
| 3,973,579 | Ollivier | 8-10-76 |
| 3,605,785 | Kobritz | 9-20-71 |
| 3,882,882 | Preisig | 5-13-75 |
| 4,085,766 | Weigle et al. | 4-25-78 |
| 4,064,891 | Eberhardt | 12-27-77 |
| 4,340,044 | Levy et al. | 7-20-82 |
| 4,336,590 | Jacq et al. | 6-22-82 |
| 3,385,295 | Beasley | 1-9-68 |
| 4,127,121 | Westenskow et al. | 4-28-78 |
| 3,362,404 | Beasley | 1-9-68 |
| 3,734,092 | Kipling | 4-22-73 |
| 3,834,383 | Weigl et al. | 9-10-74 |
| 4,044,763 | Bird | 8-30-77 |
| 4,425,805 | Ogura et al. | 1-17-84 |

U.S. Pat. No. 3,973,579 issued to Ollivier discloses an apparatus for controlling the ratio of the flow of two gases. Unit 10 senses the flow rate of a gas in an initial portion 23 of conduit 20 by coupling the gas in the initial portion 23 to the chamber 30 via passage 28. Flexible diaphragm 33, sensing the pressure in chamber 30 and hence the flow rate of the gas in the initial portion 23, controls the amount of gas introduced into the downstream portion 27 of conduit 20 from source 44 via passage 29.

U.S. Pat. No. 4,340,044 issued to Levy et al. and U.S. Pat. No. 4,366,590 issued to Jacq et al. both disclose ventilators using microprocessor control. In particular, Levy et al. discloses a microprocessor for controlling the ratio of oxygen to air in a ventilator. Levy et al. does not add oxygen as a function of the flow rate of the gas, but rather, premixes the air and oxygen in a predetermined ratio.

U.S. Pat. No. 3,385,295 issued to Beasley discloses an apparatus for use in administering intermittent positive pressure breathing therapy which uses an exhalation valve 90.

U.S. Pat. No. 4,127,121 issued to Westenskow et al. discloses an oxygen and anesthesia delivery device having an oxygen sensor 3 in a feedback loop to control the amount of oxygen injected into the main breathing line for maintaining oxygen concentration constant in the main breathing line. Westenskow, et al. adds oxygen downstream from bellows 11. Oxygen sensor 3 produces a signal to control oxygen pump 9. The oxygen and anesthesia delivery system illustrated by Westenskow, et al. comprises a closed-loop system wherein the patient 1 depletes the oxygen level during breathing. Oxygen sensor 3 produces a signal to operate oxygen pump 9 to replace oxygen depleted by the patient. Hence the nitrogen oxide and oxygen are substantially premixed in the system, as illustrated by Westenskow.

U.S. Pat. No. 3,605,785 issued to Dobritz, U.S. Pat. No. 3,882,882 issued to Preisig, U.S. Pat. No. 4,085,766 issued to Weigl, et al., and U.S. Pat. No. 4,064,891 issued to Eberhardt all disclose an apparatus for maintaining the mixture of two gases at a substantially constant ratio. The remaining patents are not as pertinent as those described above.

The above cited patents primarily disclose mechanical devices for mixing two different types of gases to maintain a substantially constant ratio by sensing differential pressure between the gases and adjusting flow based on the differential pressure. Such devices have a slow response time, are inaccurate in operation and adjust the flow in a mechanical feedback system based upon previous information, rather than looking forward to the next segment to adjust the flow based upon a desired mixing ratio for a subsequent time interval. Although Levy et al. and Jacq et al. disclose microprocessor control of ventilators and devices for controlling gas flow, the Levy et al. device does not vary the oxygen supply to coincide with a variable flow rate and Jacq et al. merely incorporates a standard feedback control system for sensing differential pressures as do the mechanical control devices cited above. Jacq et al. does not disclose the maintenance of predetermined concentrations of either of the gases.

Consequently, the prior art fails to disclose a system for regulating the flow of gas from a pressurized source to maintain a predetermined concentration in a variable flow output using predictive servo control techniques. Although various feedback control techniques have been disclosed in the prior art, including both the mechanical and electronic control, such systems fail to provide the accuracy and response time necessary in applications as required in variable flow respirators.

SUMMARY OF THE INVENTION

The present invention may therefore comprise a variable flow reciprocating piston respirator system which is capable of providing a substantial constant enrichment of oxygen throughout an inspiratory stroke comprising, a reciprocating piston respirator for producing a variable flow output, an oxygen supply for producing a supply of oxygen, a control valve for controlling flow of the oxygen from the oxygen supply, a device for combining the flow of oxygen from the control valve with the variable flow output downstream from the reciprocating piston respirator, and an airway for inducing turbulence sufficient to substantially mix the oxygen with the variable flow output from the reciprocating piston respirator.

The present invention may also comprise a method of producing a substantially constant enrichment of oxygen in a reciprocating piston respirator which uses a piston pump to produce a variable flow output comprising the steps of, determining an instantaneous flow of oxygen to produce the substantially constant enrichment of oxygen, controlling operation of a control valve to deliver the instantaneous flow of oxygen, combining the oxygen delivered by the control valve downstream from the piston pump, and inducing turbulence in an airway for delivering the variable flow output and the oxygen to a patient to substantially mix the oxygen with the variable flow output.

The advantages of the present invention are that a substantially constant percentage of oxygen can be produced in the variable flow respirator output by controlling the opening magnitude of the control valve. The opening magnitude of the control valve is calculated from a valve performance table stored in a microprocessor. The instantaneous flow of oxygen during each next segment is calculated from the percentage of the instantaneous oxygen flow of the instantaneous total flow to obtain the selected percentage of oxygen enrichment for the selected flow profile. Since the selected flow profile, percentage of oxygen and valve performance table are known by the microprocessor, the control valve signal can be generated in advance for each next segment to provide a predictive servo control mechanism using highly accurate feed forward techniques, rather than less accurate feedback techniques that have a slow response time.

The present invention also utilizes an airway to supply the variable output flow and the supply of oxygen which is specifically designed with a non-uniform inner surface to induce turbulence and mix the gases along a distance which is sufficiently long to provide a substantially uniform mixing prior to inspiration by the patient.

Flow sensor means are also provided which allow recalculation of the oxygen control valve turn-on value during each expiratory stroke to insure precise operation of the control valve. Also, an oxygen content detector is also provided in accordance with the present invention to provide feedback to detect remaining minute errors in the system and to generate an alarm signal if the air exceeds a predetermined value. Consequently, the present invention provides a precise manner of regulating the operation of the control valve using predictive servo control techniques to provide a substantially constant enrichment of oxygen in a variable flow respirator output having a preselected flow profile.

BRIEF DESCRIPTION OF THE DRAWINGS

An illustrative and presently preferred embodiment of the invention is shown in the accompanying drawings, wherein:

FIG. 3 comprises a graph illustrating locational position value versus time segments for a preselected flow profile;

FIG. 4 comprises a graph illustrating a predetermined flow profile produced by the locational position values illustrated in FIG. 3;

DETAILED DESCRIPTION OF THE PRESENT INVENTION

Figure 1:
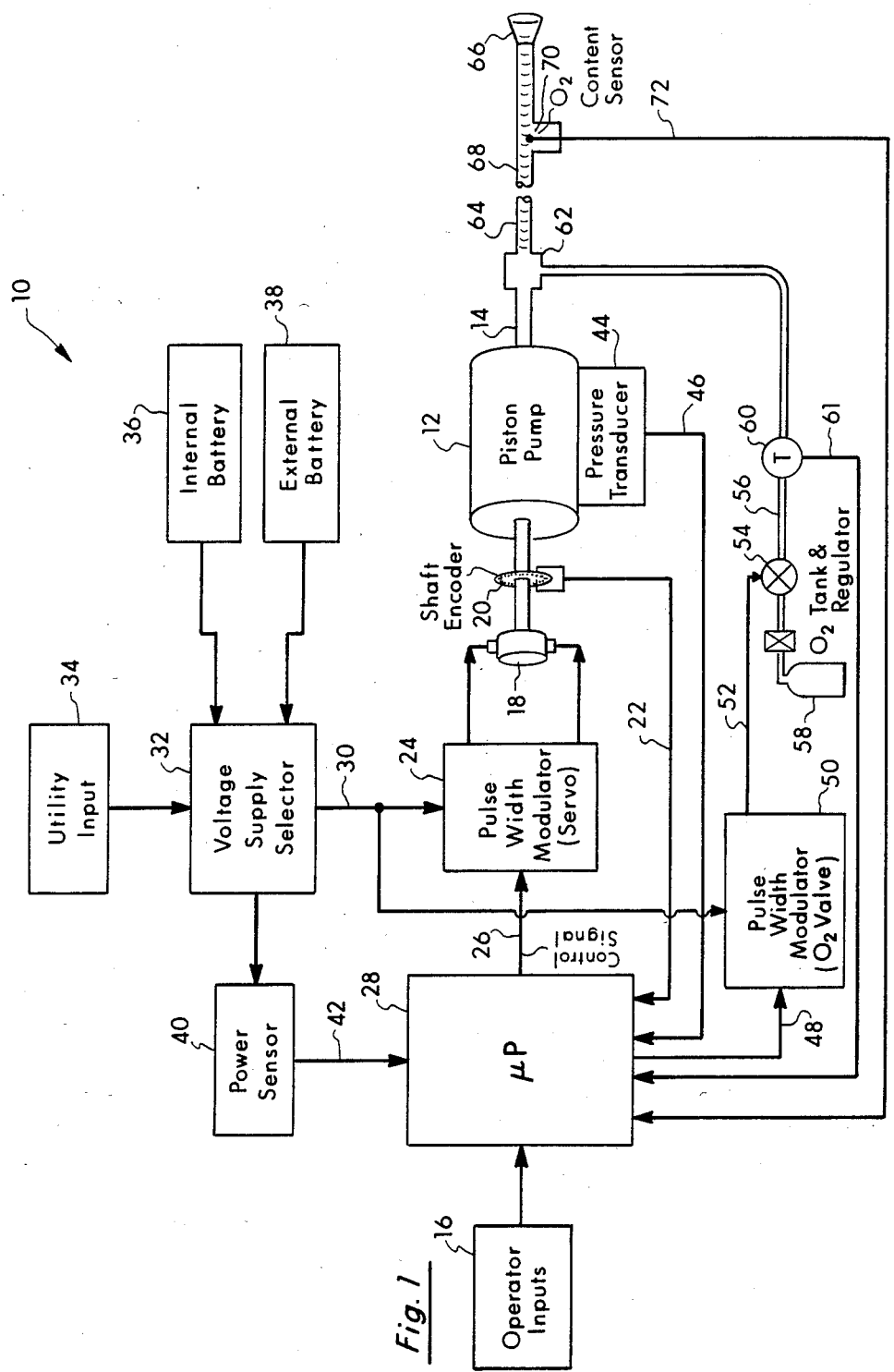
FIG. 1 comprises a schematic block diagram of the variable flow reciprocating piston respirator system of the present invention.

FIG. 1 comprises a schematic block diagram of the variable flow reciprocating piston respirator system 10 of the present invention. The reciprocating piston respirator system uses a piston pump 12 to produce a variable flow output 14 having a preselected flow profile. The preselected flow profile can comprise one of several flow profiles selected by an operator at the operator input 16. The preselected flow profile is generated by the manner in which the piston pump is operated by a drive motor 18. Shaft encoder 20 produces a signal 22 indicating the locational position of the piston within the piston pump 12. Pulse width modulator 24 produces a pulse width modulation signal having an average voltage corresponding to a predetermined torque calculated to drive the piston of the piston pump 12 to the position for the next segment time stored in the microprocessor for the selected predetermined flow profile. The pulse width modulator 24 produces the pulse width modulated signal in response to a control signal 26 produced by microprocessor 28. Pulse width modulator 24 pulse width modulates with supply voltage signal 30 from voltage supply selector 32 which provides power from either the utility input 34, the internal battery input 36, or the external battery input 38 in response to a selection signal from the microprocessor. Power sensor 40 detects the level of the voltage supply signal 30 to produce a power sensor signal 42 which is applied to microprocessor 28 to adjust control signal 26 to insure that sufficient torque is generated for the power available from the voltage supply signal 30. Operator inputs 6 provide for selection of variables pertaining to volume, flow, breath per minute, and other parameters of the system. Pressure transducer 44 senses the pressure within piston pump 12 to provide a feedback signal 46 for adjusting control signal 26.

Microprocessor 28 also produces an oxygen control output signal 48 which is applied to pulse width modulator 50. Pulse width modulator 50 pulse width modulates the power signal 30 applied to pulse width modulator 50 to produce a pulse width modulated signal 52 which is applied to control valve 54. Control valve 54 comprises a proportional valve which produces a flow of oxygen 56 from oxygen supply tank and regulator 58 proportional to the average voltage of the pulse width modulated signal 52. Oxygen supply tank and regulator 58 supply oxygen at a supply pressure substantially higher than the pressures of the variable flow output 14 produced by piston pump 12 so that the flow of oxygen through control valve 54 is not significantly affected by the variable flow output 14. Control valve 54 has a predetermined performance table which is stored in microprocessor 28. Thermistor 60 comprises a flow detector for generating an instantaneous oxygen flow signal 61 indicative of the instantaneous flow of oxygen 56 through control valve 54. A means for combining a merge chamber 62 combines the instantaneous flow of oxygen 56 with the variable flow output 14 from piston pump 12. In accordance with the present invention, the merge chamber 62 is located proximate to the output of piston pump 12. A delivery airway 64 having a predetermined length is coupled to the means for combining 62 for delivering the combined variable flow output from piston pump 12 and the flow of oxygen 56 to patient connector device 66. Delivery airway 64 has a non-uniform inner surface 68 which generates turbulence within delivery airway 64 sufficient to cause substantial mixing of the gases within the predetermined length of airway 64. Oxygen content sensor 70 is coupled to the delivery airway 64 adjacent the patient connector device 66 to generate an oxygen content signal 72 which is applied to microprocessor 28. Oxygen content signal 72 comprises a feedback signal which indicates the actual percentage of oxygen in the total flow coupled to the patient through patent connecting device 66.

Figure 2:
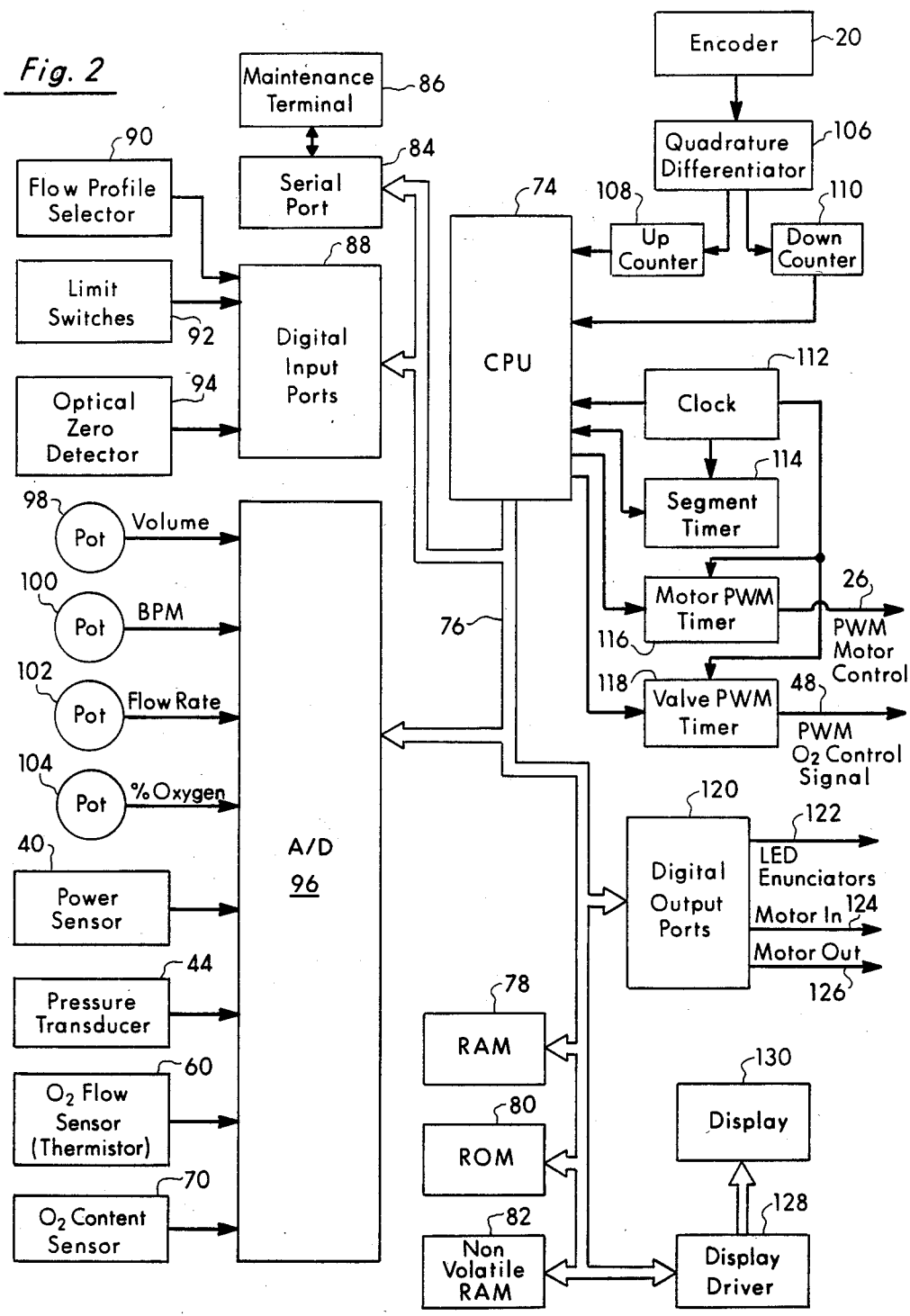
FIG. 2 comprises a detailed block diagram of the microprocessor and associated elements of the present invention.

FIG. 2 is a detailed block diagram of the microprocessor 28 and associated circuitry. The heart of the microprocessor 28 is a central processing unit 74 which is coupled to a bus 76. Bus 76 is coupled to random access memory (RAM) 78, read only memory 80, and non-volatile RAM 82 which comprise the supplemental memory of the microprocessor. Bus 76 is also coupled to serial port 84 which is in turn connected to a maintenance terminal 86 for entering parameter data into central processing unit 74. Digital input ports 88 receive data from flow profile selector 90, limit switches 92 and optical zero detector 94. Flow profile selector 90 provides a digital input for selecting a predetermined flow profile from one of several flow profiles stored in the microprocessor 28. Limit switches 92 indicate if the piston has exceeded a predetermined location within the piston pump 12. Optical zero detector 94 provides a position signal for locating the piston within the piston pump at the end of each stroke. Digital input ports 88 couple the inputs to bus 76. Analog inputs are converted to digital inputs for bus 76 in A to D converter 96. Volume POT 98 produces an analog signal indicative of the volume selected by the operator for the inspiratory stroke of piston pump 12. Similarly, breath per minute pot 100 produces an analog signal indicative of the desired breaths per minute. Flow rate pot 102 produces an analog signal dicative of the peak flow rate to be produced. Percent oxygen potentiometer 104 produces an analog signal indicative of the desired percentage of oxygen to be supplied by the reciprocating piston respirator system. Power sensor 40, pressure transducor 44, $O_2$ flow sensor, comprising thermistor 60, and $O_2$ content sensor 70 are each applied to the A to D converter 96 for digitizing and application to bus 76. Encoder 20 produces an encoder signal which is applied to quadrature differentiator 106 for differentiating the phases of the encoder signal and application to up-counter 108 and down-counter 110. Counts accumulated in counter 108 indicate a rotational position of the shaft with regard to a reference in a first direction, while the counts accumulated in down-counter 110 indicate a rotation of the shaft from a predetermined reference in a second direction. The outputs of up-counter 108 are accessible to CPU 74 through BUS 76. Clock 112 produces a clock signal which is applied to segment counter 114, motor PWM timer 116, valve PWM timer 118, and CPU 74. Segment timer 114 provides an indication of the segment time for the selected breath per minute value. Counter/timer 116 produces a control signal 26 conmprising a pulse width modulated motor control signal for controlling the torque produced by motor 18. Control signal 48 comprises a pulse width modulated oxygen control signal for regulating the control valve to insure that the flow of oxygen from the control valve produces a substantially constant enrichment of oxygen in the respirator output. The counter/timers are also BUS resident devices.

Digital output ports 120 produce output signals including output signal 122 to LED enunciators to indicate operation of the system. Additionally, output ports 120 produce a motor-in signal 124 and a motor-out signal 126 indicating the direction of movement of motor 18. Display driver 128 is coupled to bus 76 to produce a display signal for a display 130 which can comprise a liquid crystal display. Display 130 provides information regarding operation of the system.

FIG. 3 is a graph of the locational position values for a predetermined flow profile versus segment times. As illustrated in FIG. 3, plot 132 indicates the series of successive locational position values of the piston within the piston pump 28 for a plurality of substantially equal segment times. The area under curve 132 comprises the volume displaced by the piston during an inspiratory stroke. The total distance moved by the piston comprises the total differential position value 134. The period between each segment time comprises a time interval 136. As the piston moves in piston pump 28 it assumes the positions indicated by plot 132 at each of the segment times. This is achieved by the production of a predetermined torque in motor 18 as a result of the pulse width modulated signal produced by pulse width modulator 24 in response to control signal 26 produced by microprocessor 28. Microprocessor 28 utilizes a predictive servo control technique to generate control signal 26. Assuming the piston has reached a current position 138 on curve 132 at a current segment time 144 equal to 6, the current locational position value of the piston is approximately 8. Microprocessor 28 then determines the position 140 on curve 132 for next segment 148 which the piston must assume at next segment time 146 which is equal to 7. The difference in the locational position values for the current position 138 and the position at the next segment time 140 comprises a differential locational position value 142. Curve 132 is generated within the microprocessor to produce a total volume corresponding to the selected input volume, and flow corresponding to the breath per minute rate and peak flow value, to provide a substantially constant enrichment of oxygen corresponding to the operator selected enrichment value and to produce the selected flow profile.

FIG. 4 comprises a graph of flow velocity versus segment times which illustrates the flow profile produced by curve 132 of FIG. 3. As illustrated in FIG. 4, variable flow respirator output 150 comprises the flow profile produced at patient connector 66 which includes both the variable flow output 14 from piston pump 12 and the flow of oxygen 56 from control valve 54. The curve 56 illustrates the flow of oxygen combined with the variable flow output 14 to produce the variable flow respirator output 150. Operator inputs 16 generate information regarding the flow profile of the variable flow output 14 and flow of oxygen 56 must be adjusted to produce the variable flow respirator output 150 having a preselected flow profile and a constant percentage of oxygen selected by the operator.

Figure 5:
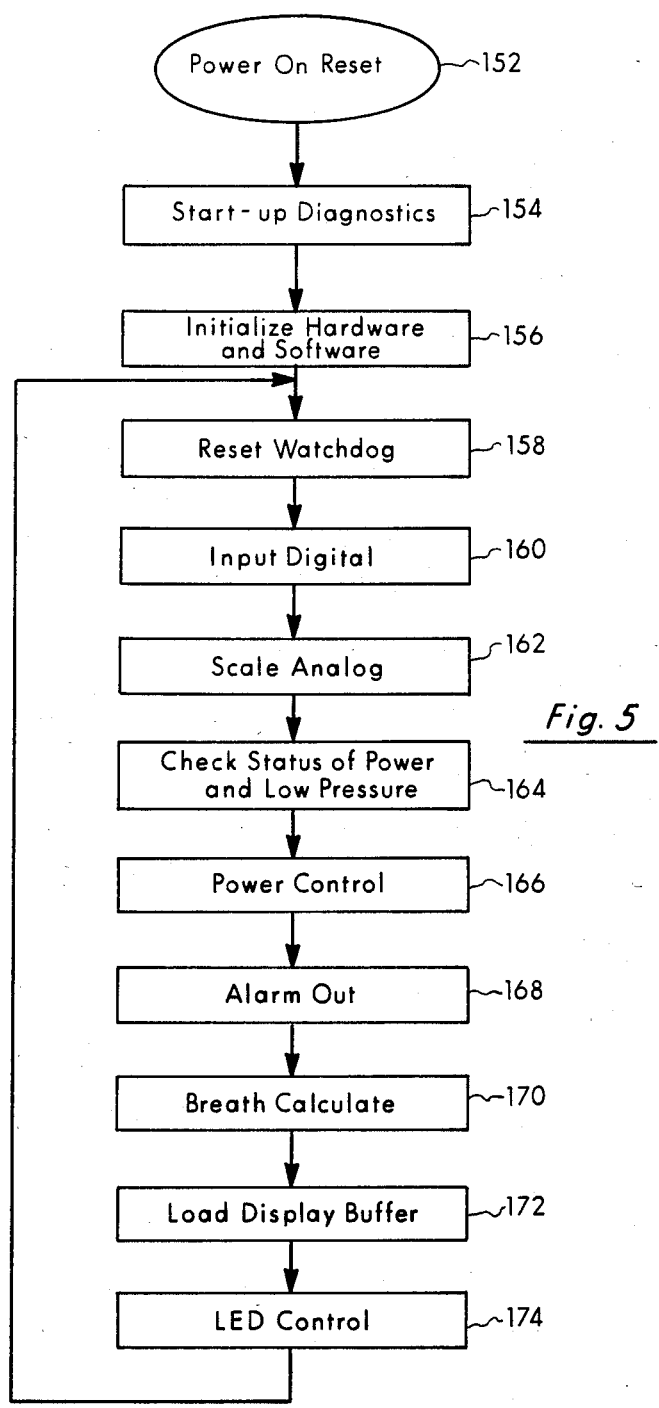
FIG. 5 is a schematic flow diagram of the main operational program of the microprocessor of the present invention.

FIG. 5 comprises a flow diagram of the operating program for the microprocessor illustrated in FIG. 2. The power-on reset function 152 functions to reset the hardware. Start-up diagnostics 154 proceed through the diagnostic system and indicate to the operator the operational condition of the system. For example, each of the LED's is flashed to indicate that they are working. Additionally, the LCD display is operated to show its working condition. The initialized hardware and software step 156 functions to clear the registers so that the microprocessor can operate from a known state. The reset watch dog step 158 is a safety step for triggering operation of the microprocessor if it has gone into a stop mode. The input digital step 160 functions to read the flow profile selector 90, limit switches 92 and optical detector 94, as illustrated in FIG. 2. The scale analog step 162 sets up ADC 96 to periodically read front panel potentiometers 98, 100, 102, 104, power sensors 40, pressure transducer 44, $O_2$ flow sensor 60, and $O_2$ content sensor 70. Each analog input is read about ten times per second. The check status of power and low pressure step 164 checks the input power supply from the power sensor 40 and determines the power available. The power control step 166 selects the source of power to be used by the system. Alarm out step 168 reads the status of the entire system and determines if an alarm is necessary. Breath calculate step 170 reads the parameter inputs of the systems and performs arithmetic operations. Load display buffer 172 reads the operational values of the systems and feeds these values to the operator by way of display driver 128. LED control step 174 reviews the data base status and controls the LEDs to be lit. The program then recirculates to the reset watchdog step 158.

Figure 6:
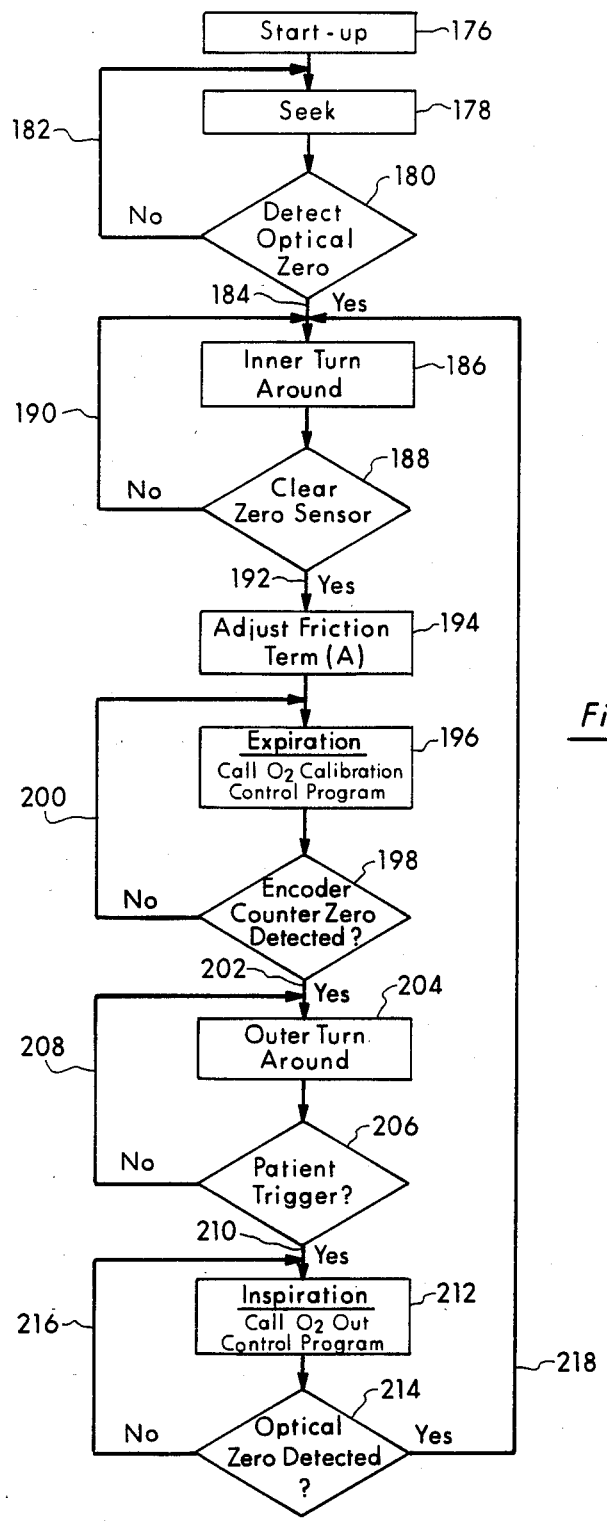
FIG. 6 is a schematic flow diagram of the piston control program performed by the microprocessor of the present invention.

The piston operation program is schematically illustrated in the flow chart disclosed in FIG. 6. The program begins with a start-up step 176 which initializes the program. The program then proceeds to a seek step 178 which moves the piston in a forward direction. Decision block 180 detects whenever the optical zero signal has been produced by optical zero detector 94. If the optical zero detector 94 has not produced a signal, the program remains in the seek step 178 by way of return loop 182 to continue moving the piston with constant torque. As soon as the optical zero mark is detected, the program moves to the inner turn around step 186 via "Yes" path 184 which stops the drive motor 18 and produces a reverse torque in the motor to drive it away from the bulkhead.

The program then proceeds to the cleared zero sensor decision step 188 to detect if optical zero detector 94 has ceased producing a signal to indicate that the piston has cleared the optical zero detector as a result of the application of reverse torque in the inner turn around step 186. If optical zero detector 94 is producing a signal, the program recirculates to inner turn around step 186, as indicated by feedback loop 190. As soon as the piston clears the zero point, the program proceeds to the adjust friction term step 194 via "Yes" path 192 which functions to adjust the static friction term of the torque equation. The "A" term comprises the only free standing constant of the system and is adjusted at step 194 at the beginning of each stroke to compensate for differences in the predicted movement to the actual movement of the piston.

Figure 7:
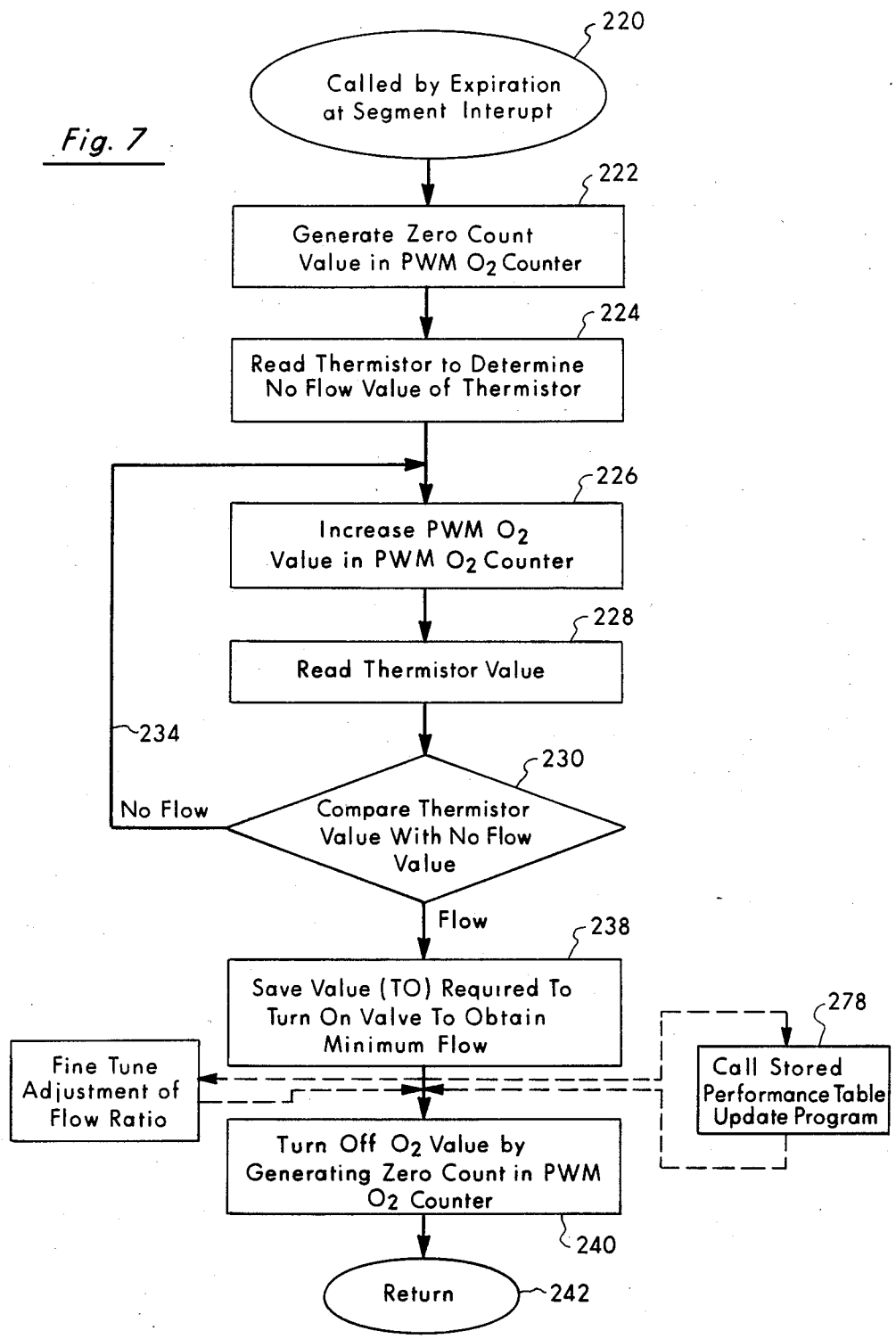
FIG. 7 is a schematic block diagram of the $O_2$ calibration control program of the present invention.

The program then proceeds to the expiration cycle 196 and calls the oxygen calibration program disclosed in FIG. 7 while the piston is being pulled back. This is required because flow of the valve is very sensitive to $O_2$ tank source pressure. The program then proceeds to the encoder counter zero detected decision block 198 which detects if motor PWM timer 116 has reached a full loaded value indicating that the piston has moved a predetermined distance within the reciprocating piston respirator. The full volume to be delivered, which is selected on potentiometer 98 in conjunction with POT 104 is loaded as a predetermined count in down counter 110. When the piston has moved to the preselected distance the encoder will have documented down counter to a zero value, indicating that the correct piston position has been attained. If not, the program recycles to expiration step 196 by way of return loop 200. When the proper correct piston position is detected on downcounter 110, the program proceeds to outer turn around step 204 via "Yes" path 202 which stops the motor. The program then proceeds to the patient trigger decision box step 206 to determine if a patient trigger has been received to proceed with the movement of the piston. The patient trigger can be produced by an inspiratory effort by the patient or an automatic trigger provided by the system. If no trigger has been received, the piston remains in a stopped or paused position as indicated by return loop 208. As soon as the patient trigger is received the program proceeds to the inspiration step 212 via "Yes" path 210 which calls the servo control. Once the servo control program is completed the piston control program proceeds to decision block 214 to determine if the optical zero has been detected. If it has not, it recirculates to the inspiration step 212 by way of return loop 216. If the optical zero has been detected, the program then proceeds to the inner turn around step 186 by way of return loop 218.

FIG. 7 comprises a flow diagram of an oxygen calibration control program which is called by the expiration step of the piston control program. During the expiration cycle, a calibration reading is made from the thermistor 60 to set the turn-on level of control valve 54. The first step in the program illustrated in FIG. 7 is to call the program at step 220 from the expiration step at the segment interrupt time. The program then proceeds to generate a zero count value in the pulse width modulator oxygen counter (valve PWM timer 118) step 222 causing control valve 54 to close and preventing the flow of oxygen from oxygen tank 58. The program then proceeds to read the thermistor 60 at step 224 to determine the no flow value produced at output 61. The program increases the value in counter time 118 at step 226 and simultaneously reads the thermistor value at step 228. The thermistor value is monitored and compared at step 230 with the thermistor no flow value to determine if oxygen is flowing. The program recycles at return loop 234 to continue to increase the count until oxygen flow is experienced. The program saves the value (TO) required to turn on the valve at step 238 and then proceeds to step 240 to generate a zero count in valve PWM timer 118 to close control valve 54. The program then returns at step 242 to the expiration step in the servo control program.

Figure 8:
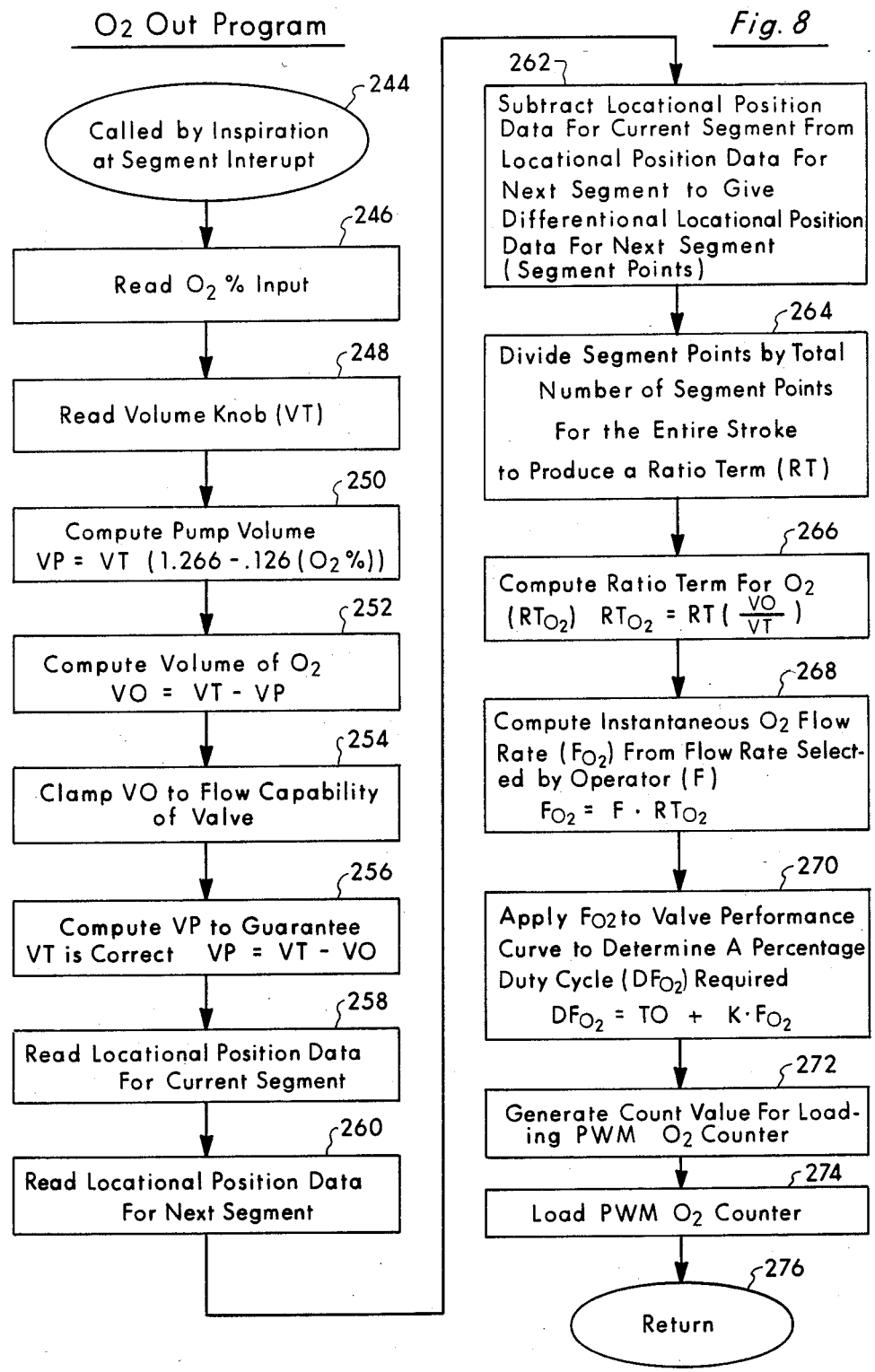
FIG. 8 is a schematic flow diagram of the $O_2$ out program of the present invention.

FIG. 8 comprises the $O_2$ out program which generates the count in valve PWM timer 118 during the inspiration portion of the stroke to produce the flow of oxygen 56 which can be combined with the variable flow output 14 to produce the variable flow respirator output 150 so that a preselected flow profile is produced with the proper volume, shape and period and having a substantially constant enrichment of oxygen considering the oxygen available in the variable flow output 14. The $O_2$ out program is called by the inspiration step at segment interrupt time from the servo control program illustrated in FIG. 6, as indicated by step 244. The program then proceeds to read the oxygen percentage input from potentiometer 104 at step 246 which is indicative of the desired percentage of oxygen in the variable flow respirator output 150 including oxygen available in the variable flow output 14. The program reads the volume potentiometer 98 at step 248 to obtain a total volume signal (VT). The program proceeds to compute the pump volume at step 250 using the illustrated algorithm. The pump volume comprises the volume of the variable flow output 14 produced by piston pump 12. The algorithm is derived by knowing that air typically contains approximately twenty-one percent oxygen. Consequently we can say that the percentage of oxygen in the variable flow respirator output 150 is equal to the volume of oxygen in the variable flow output 14 plus the volume of oxygen provided by the supply of oxygen 58 divided by the total volume. This can be expressed as $$O_2\% = (0.21 VP + VO)/VT \quad (1)$$

It is also known that the total volume is equal to the volume provided by the piston pump plus the volume provided by the oxygen enrichment source 58. This can be expressed as:

$$VT = VP + VO \quad (2)$$

Solving equation 1 for VO and inserting that into equation 2 and solving the resultant equation for VP gives the equation for pump volume in terms of the total volume and the percentage of oxygen as illustrated below:

$$VP = VT[1.266 - 0.126\ (O_2\%)] \quad (3)$$

Equation 3 therefore gives the volume to be produced by piston pump 12 during the next inspiratory stroke. Once the piston pump volume (VP) is known from equation 3 the volume of oxygen (VO) can be computed from equation 2. This is performed in step 252 in the $O_2$ out program illustrated in FIG. 8. The volume of oxygen (VO) is then clamped to the flow capabilities of control valve 54 to determine if the value is within the range of operable values to produce the desired flow of oxygen, as disclosed in step 254. The program then proceeds to step 256 to compute the pump volume (VP) to guarantee that the total volume (VT) is correct, again using equation 2. The program then proceeds to step 258 to read locational position data for the current segment. In other words, the program reads the locational position value for a current position 138 (FIG. 3) for a selected flow profile 132. At step 260 the program reads the locational position data for the next segment which comprises the locational position value at the next segment time 146, comprising the position 140 which the piston must assume at the next segment time 146. The program then proceeds to step 262 to subtract the locational position values for the current position 138 and the position 140 at the next segment time 146 to generate a differential locational position value 142. This differential locational position value 142, which is denoted as "segment points," is divided by a total differential position value 134 (FIG. 3) to produce a ratio term (RT), as disclosed in step 264. The program then proceeds to step 266 to compute the ratio term for oxygen ($RT_{O2}$) which comprises the ratio term (RT) times the volume of oxygen (VO) divided by the total volume (VT). The instantaneous oxygen flow rate ($F_{O2}$) is then computed at step 268 from the flow rate selected by the operator, as illustrated in step 268. The program then proceeds to step 270 to apply the instantaneous oxygen flow rate ($F_{O2}$) to a valve performance curve stored in microprocessor to determine a percentage duty cycle ($DF_{O2}$) for oxygen. Control valve 54 constitutes a proportional valve that produces a substantially linear output having a predetermined slope K plus an offset value which comprises the turn-on value (TO). Consequently, the duty cycle ($DF_{O2}$) is equal to the turn-on value computed in the oxygen calibration control program, illustrated in FIG. 7, plus an empirically derived constant K times the instantaneous oxygen flow rate ($F_{O2}$) as illustrated at step 270. The program then proceeds to generate a count value for loading the pulse width modulator $O_2$ counter comprising counter timer 118 with a count corresponding to the duty cycle ($DF_{O2}$) at step 272. The program proceeds to step 274 to load valve PWM timer 118 with the count value generated in step 272. The program returns at step 276 to the inspiratory step 212 of the servo control program illustrated in FIG. 6.

Figure 9:
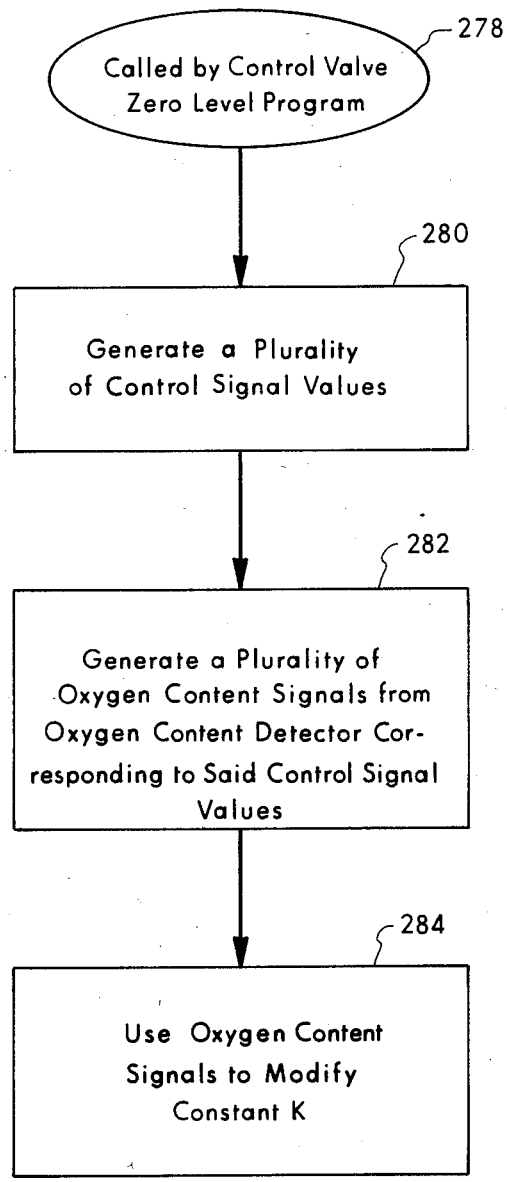
FIG. 9 is a schematic flow diagram of the stored performance table update program of the present invention.

Referring to the control valve zero level program illustrated in FIG. 7, step 278 can alternatively be incorporated within the program between step 238 and 240 to call the stored performance table update program illustrated in FIG. 9. The stored performance table update program comprises a means for adjusting the constant K for control valve 54. As illustrated in FIG. 9, at step 278 the program is called from the control valve zero level program. The program generates a plurality of control signal values in counter timer 118 during the expiratory stroke, as illustrated in step 280. The program then generates a plurality of oxygen content signals from oxygen content sensor 70 corresponding to the control signal values at step 282. These oxygen content signals, together with the control signal values, are then used to modify the constant K at step 284.

Figure 10:
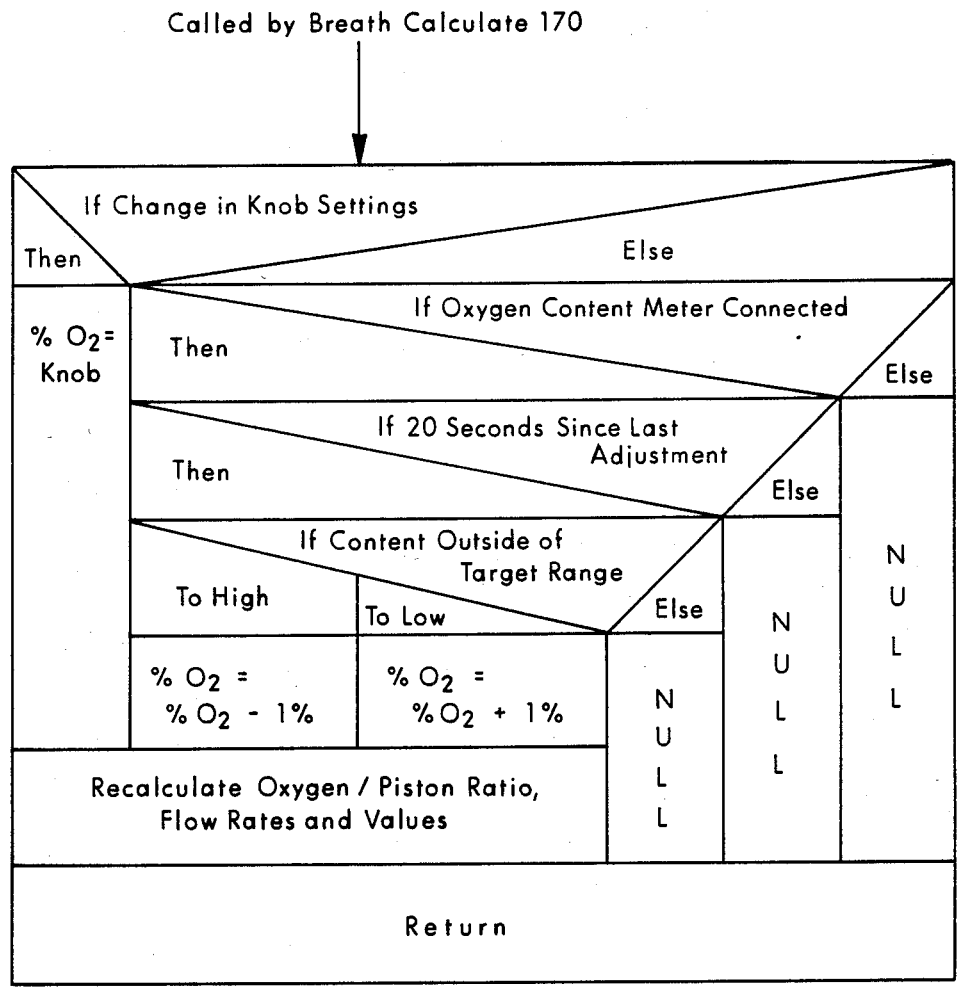
FIG. 10 is a flow diagram disclosing the manner in which oxygen is monitored and used to fine tune the oxygen content output.

FIG. 10 discloses a flow diagram describing the manner in which oxygen is monitored to produce a feedback signal to fine tune the content of oxygen in the output. The program illustrated in FIG. 10 is called by the breath calculate step 170 of the main operational program illustrated in FIG. 5. The program determines if changes have been made in the knob settings, if the oxygen content meter is connected, if a twenty second waiting period has elapsed, if the oxygen conent is outside of the target range. The oxygen is then adjusted in either an upward or downward direction. The oxygen/piston ratio flow rates and volumes are then recalculated. These steps are performed in conjunction with the oxygen content sensor 70 which is used to adjust the ratio of VO/VP until the information represented by the content sensor 70 represents the same value as preset by the operator on the % oxygen POT 104. If adjustment in the ratio of VO/VP does not give the desired variable flow respirator output 150 at ventillator output 66, then an alarm is activated.

Consequently, the present invention provides a variable flow reciprocating piston respirator system which is capable of providing a substantially constant enrichment of oxygen in a variable flow respirator output. This is achieved by controlling the operation of a proportional control valve to produce an instantaneous flow of oxygen which supplements a variable flow output from a piston pump to produce a substantially constant enrichment with the selected volume and selected flow profile. The oxygen is added downstream from the piston pump to improve safety and reduce health hazards. A delivery airway is utilized having a nonuniform inner surface which generates sufficient turbulence to produce substantial mixing of the gases prior to inspiration by a patient. The present invention utilizes predictive servo control techniques to generate control signals to operate control valve 54 and piston pump 12 for each subsequent successive segment which provides for a highly accurate manner of producing a substantially constant enrichment in a variable flow respirator output in a highly responsive manner not previously achievable by conventional feedback control techniques. 1

These principles can also be extended for use in mixing gases other than oxygen or in addition to oxygen. Some other gases to be mixed might include anesthetic, humidification and nebulized medications.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited To the particular use contemplated. It is intended that the appended claims be construed to include other alternative embodiments of the invention except in so far as limited by the prior art.

What is claimed is:

1. A variable flow reciprocating piston respirator system which is capable of providing a substantially constant supply gas enrichment of a reciprocating piston gas produced by said reciprocating piston respirator throughout an inspiratory stroke of said reciprocating piston respirator comprising:
   reciprocating piston respirator means for producing a variable flow output of said reciprocating piston gas;
   supply gas reservoir means for providing a source of said supply gas to be admixed with said reciprocating piston gas;
   control valve means for regulating flow of said supply gas from said supply gas reservoir means;
   means for combining said flow of said supply gas from said control valve means with said variable flow output of said reciprocating piston gas downstream from said reciprocating piston respirator means; and,
   airway means for inducing turbulence sufficient to substantially mix said supply gas with said variable flow output of said reciprocating piston gas from said reciprocating piston respirator means;
   logic means for generating a control signal for regulating said control valve means such that said flow of said supply gas from said control valve means produces said substantially constant supply gas enrichments.

2. The respirator of claim 1, wherein said logic means comprises:
   means for computing said control signal from a valve performance table which indicates a control signal value for providing an instantaneous predetermiined flow of said supply gas computed to supplement said variable flow output of said reciprocating piston gas to produce a variable flow respirator output having a total selected volume and selected percentage of supply gas enrichment which is substantially constant throughout said inspiratory stroke considering a percentage content oxygen present in said variable flow output.

3. The respirator at claim 2 further comprising:
   supply gas detector means for detecting an actual percentage of said supply gas delivered by said variable flow reciprocating respirator system and generating a feedback signal representative of said actual percentage of said supply gas.

4. The respirator of claim 2 further comprising:
   means for entering operational parameters of said variable flow reciprocating piston respirator system including said selected volume and said selected percentage of enrichment.

5. The respirator of claim 2 further comprising:
   flow detector means for generating a flow signal indicative of said flow of said supply gas from said control valve means;
   means for computing a turn-on value for said control valve means during an expiratory stroke by detecting a minimum control value signal to produce said flow signal from said flow detector means.

6. A system for providing a substantially constant oxygen enrichment in a variable flow reciprocating piston respirator comprising:

piston pump means for producing a variable flow output;

oxygen supply means for providing a flow of oxygen at a supply pressure substantially higher than pressures of said variable flow output produced by said piston pump means for combination with said variable flow output downstream from said piston pump means;

control valve means for regulating said flow of oxygen from said oxygen supply means; and, microprocessor means for generating a instantaneous oxygen flow signal to control operation of said control valve means such that said control valve means produces an instantaneous flow of oxygen resulting in a variable flow respirator output having an oxygen enrichment which remains substantially constant for an inspiratory stroke and a flow profile and volume corresponding to a preselected flow profile and volume.

7. The system of claim 6 further comprising:

volume entry means for entering said preselected volume representative of a total volume (VT) of said variable flow respirator output;

breath per minute entry means for entering a breath per minute rate to be delivered by said variable flow reciprocating respirator;

flow rate entry means for entering a peak flow rate to be delivered by said variable flow reciprocating respirator;

oxygen percentage entry means for entering a substantially constant percentage of oxygen enrichment to be delivered by said reciprocating piston respirator;

flow profile entry means for entering said preselected flow profile.

8. The system of claim 7 wherein said microprocessor means comprises:

means for computing a pump volume (VP) to be delivered by said piston pump means using said total volume (VT) entered through said volume entry means and said percentage of oxygen enrichment entered through said oxygen percentage entry means;

means for computing a volume of oxygen (VO) to be delivered by subtracting said pump volume (VP) from said total volume (VT);

means for computing locational position data indicative of a plurality of successive positions a piston must assume in said piston pump at a plurality of successive substantially equal segment times to produce a preselected flow profile;

means for computing a ratio term (RT) indicative of a percentage of movement of said piston during a next segment compared to total movement at said piston during said inspiratory stroke;

means for computing a ratio term for oxygen ($RT_{O2}$) by multiplying said ratio term (RT) by the quotient of VO divided by VT;

means for computing an instantaneous total flow (F) for said next segment;

means for computing an instantaneous flow of oxygen ($F_{O2}$) for said next segment by multiplying said instantaneous total flow (F) by said ratio term for oxygen ($RT_{O2}$);

means for generating said instantaneous oxygen flow signal for opening said control valve means to produce said instantaneous flow of oxygen at a flow rate substantially equal to $F_{O2}$ by computing and opening magnitude for said control valve from a control valve performance table stored with said microprocessor means.

9. The respirator of claim 6 further comprising:

flow detector means for generating a flow signal indicative of said flow of oxygen from said control valve means;

means for computing a turn-on value for said control valve means during an expiratory stroke by detecting a minimum control value signal to produce said flow signal from said flow detector means.

10. The system of claim 8 further comprising:

oxygen detector means for detecting an actual percentage of oxygen delivered by said reciprocating piston respirator and generating a feedback signal representative of said actual percentage of oxygen delivered to said reciprocating piston respirator;

means for modifying said stored performance table for said control valve based upon said feedback signal.

11. A method of producing a substantially constant oxygen enrichment in a reciprocating piston respirator which uses a piston pump to produce a variable flow output comprising the steps of:

determining an instantaneous flow of oxygen to produce said substantially constant oxygen enrichment;

controlling operation of a control valve to deliver said instantaneous flow of oxygen;

combining said oxygen delivered by said control valve downstream from said piston pump;

inducing turbulence in an airway for delivering said variable flow output and said oxygen to a patient to substantially mix said oxygen with said variable flow output.

12. A method of producing a proportionally substantially constant preselected percentage of oxygen in a variable flow reciprocating piston respirator system comprising the steps of:

computing a pump volume (VP) to be delivered by said variable flow reciprocating piston respirator system using a total preselected volume (VT) to be delivered and said substantially constant preselected percentage of oxygen considering oxygen present in said pump volume (VP);

computing a volume of oxygen (VO) to be delivered by an oxygen supply by subtracting said pump volume (VP) from said total preselected volume (VT);

computing a differential locational position value for a next segment by subtracting a locational position value for a next segment time from a locational position value for a current segment time;

computing a ratio term (RT) by dividing said differential position value by a total number of locational position valves for an entire stroke;

computing a ratio term for oxygen ($RT_{O2}$) by multiplying said ratio term (RT) by the quotient of VO divided by VT;

computing an instantaneous flow of oxygen ($F_{O2}$) by multiplying said ratio term for oxygen ($RT_{O2}$) by an instantaneous total flow (F);

generating a control signal for opening a control valve to deliver oxygen at a flow rate substantially equal to $F_{O2}$ by computing an opening magnitude from a stored performance table for said control valve.

13. The method of claim 13 further comprising the steps of:

reducing said control signal during expiratory strokes to close said control valve;

detecting an oxygen content output signal from an oxygen content detector while said valve is closed;

increasing said control signal during said expiratory strokes until said oxygen content detector indicates a flow of oxygen to produce an oxygen control valve turn-on value;

storing said oxygen control valve turn-on value for use in said stored performance table.

14. The method of claim 13 further comprising the steps of:

generating a plurality of control signal values to open said valve by a predetermined opening magnitude during said expiratory strokes;

generating a plurality of oxygen content signals from said oxygen content detector corresponding to said control signal values;

storing said plurality of oxygen content signals and said oxygen control valve turn-on value to modify said stored performance table for said control valve.

15. The method of claim 12 further comprising the steps of:

inserting said oxygen delivered by said control valve into said variable flow reciprocating piston respirator downstream from a piston pump;

inducing turbulence in a delivery airway sufficient to substantially mix said oxygen delivered by said control valve with gases produced by said piston pump prior to inspiration.

16. The method of claim 15 wherein said step of inducing turbulence in said delivery airway comprises the step of:

providing a non-uniform inner surface on said patient airway to induce said turbulence.

17. The method of claim 12 further comprising the step of:

generating a servo control signal to move said piston said differential locational position value.

* * * * *